US006464962B2

(12) United States Patent
Heckendorn et al.

(10) Patent No.: US 6,464,962 B2
(45) Date of Patent: *Oct. 15, 2002

(54) N-ALKYLDIETHANOLAMINE HYDROFLUORIDES AND ORAL HYGIENE COMPOSITIONS CONTAINING THEM

(75) Inventors: René Heckendorn; Jacques Gosteli, both of Basel (CH)

(73) Assignee: GABA International AG, Munchenstein (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/308,380
(22) PCT Filed: Nov. 17, 1997
(86) PCT No.: PCT/CH97/00435
§ 371 (c)(1),
(2), (4) Date: Aug. 4, 1997
(87) PCT Pub. No.: WO98/22427
PCT Pub. Date: May 28, 1998

(65) Prior Publication Data

US 2001/0006622 A1 Jul. 5, 2001

(30) Foreign Application Priority Data

Nov. 18, 1996 (CH) .............................................. 2843/96

(51) Int. Cl.⁷ ................................................ A61K 7/16
(52) U.S. Cl. ............................. 424/49; 424/52; 424/54; 433/217.1
(58) Field of Search ............................... 424/49, 52, 54; 106/35; 433/217.1

(56) References Cited

U.S. PATENT DOCUMENTS

| 3,083,143 A | * | 3/1963 | Schmid et al. ................. 167/93 |
| 3,983,175 A | | 9/1976 | Tamai et al. ................. 260/591 |
| 4,122,162 A | * | 10/1978 | Muehlemann et al. ......... 424/52 |
| 4,160,022 A | | 7/1979 | Delaney et al. ............... 424/52 |
| 5,980,868 A | * | 11/1999 | Homola et al. ............... 424/54 |

FOREIGN PATENT DOCUMENTS

| CA | 548096 | 10/1957 |
| FR | 1066270 | 6/1954 |
| GB | 1130905 | 10/1968 |

OTHER PUBLICATIONS

"Ullman's Encyclopedia of Industrial Chemistry", vol. A 10, pp. 176–177.
"Römpp Chemielexikon", 9th Edition, vol. 2, p. 1337.

* cited by examiner

*Primary Examiner*—Ralph Gitomer
(74) *Attorney, Agent, or Firm*—Leydig Voit & Mayer, Ltd

(57) ABSTRACT

Amine hydrofluorides of the general formula (I):

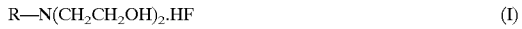

R—N(CH$_2$CH$_2$OH)$_2$.HF     (I)

In which R is a straight-chain hydrocarbon residue having 10 to 20 carbon atoms exhibit antibacterial and caries-prophylactic activity and can be prepared in high purity. The amine hydrofluorides of the formula (I) can be formulated, optionally in combination with tin fluoride, into oral hygiene compositions such as toothpastes, mouthwashes or chewable tablets.

19 Claims, No Drawings

N-ALKYLDIETHANOLAMINE HYDROFLUORIDES AND ORAL HYGIENE COMPOSITIONS CONTAINING THEM

The present invention relates to amine hydrofluorides and mixtures of these amine hydrofluorides, and to a process for the preparation of these amine hydrofluorides and their use in oral hygiene compositions.

It is known that oral hygiene compositions, by their cleaning action, make a contribution to the hygiene of the oral cavity and thus to the preservation of the health of teeth and gums. The cleaning action of these oral hygiene compositions is customarily supplemented by admixture of active compounds which prevent or control pathological symptoms in the oral cavity, in particular also the formation of bacterial films on the teeth (plaque). These films consist of polysaccharides, primarily of dextrans. In addition to the low-molecular weight sugars, these polysaccharides form a source of nutrition for the plaque bacteria (mainly streptococci and lactobacillaceae). The plaque bacteria gradually break down the polysaccharides to form acidic degradation products (e.g. pyruvic acid, lactic acid etc.). The pH decrease resulting therefrom brings about the degradation of the tooth enamel known as caries.

It has therefore already been attempted to take steps against the formation of pathological symptoms in the oral cavity using various oral hygiene compositions comprising antibacterially active substances (e.g. toothpastes, rinsing solutions or dental gels). Active compounds already known from the prior art are N-octadeca-9-enylamine hydrofluoride (international non-proprietary name "dectaflur") and in particular N'-octadecyl-N',N,N-tris(2-hydroxyethyl)-1,3-propanediamine dihydrofluoride (international non-proprietary name "olaflur"). On oral use of the hygiene composition, these active compounds form a thin hydrophobic film on the tooth enamel, the amine hydrofluoride groups coming into contact with the tooth enamel. Thus on the one hand the tooth enamel becomes more resistant to acid attacks on account of the $CaF_2$ covering layer formed, on the other hand the long-chain hydrocarbon residues form a hydrophobic layer which prevents the formation of deposits and the attack of the acidic degradation products on the tooth enamel.

The synthesis of olaflur starts from bovine tallow, a fat having a high stearic acid content. The ester groups are hydrolysed, the free fatty acids are converted into the corresponding amides using ammonia and these are dehydrated to the nitrites. Catalytic reduction thereof yields a mixture of primary fatty amines with the main constituent octadecylamine. Reaction with acrylonitrile and catalytic re-reduction affords N-octadecyl-1,3-propanediamine, which is hydroxyethylated using ethylene oxide. Amounts of by-products are formed here, as the amino groups are in some cases under- or over-substituted. The hydroxyethyl groups introduced can also be etherified by means of further ethylene oxide. The subsequent double hydrofluoridation yields the final product olaflur in technical purity, in which N'-octadecyl-N',N,N-tris(2-hydroxyethyl)-1,3-propanediamine dihydrofluoride occurs as the main component. The purification of the by-products is dispensed with for cost reasons.

The presence of these by-products was until now not considered to be inconvenient, since in relation to the film formation on the enamel they are of secondary importance. However, it has to be taken into account that in the course of the global tightening of the official approval procedures for pharmaceutical active compounds in future the marketing authorizations for contaminated active compounds will be more difficult to obtain.

The present invention is based on the object of providing active compounds which have an activity comparable with olaflur, but contain less by-products and are simpler to prepare.

The object set is achieved according to the invention by amine hydrofluorides of the general formula (I):

R—N(CH$_2$CH$_2$OH)$_2$.HF (I)

where R is a straight-chain hydrocarbon residue having 10 to 20 carbon atoms.

It has namely been found that these amine hydrofluorides and mixtures of two or more thereof have an antibacterial activity which is very similar to that of the N'-octadecyl-N',N,N-tris(2-hydroxyethyl)-1,3-propanediamine dihydrofluoride from the already-known olaflur. The antibacterial action manifests itself in the inhibition of the growth of a multiplicity of micro-organisms, for instance of *Aspergillus niger, Candida albicans, Escherichia coli, Pseudomonas aeruginosa, Staphylococcus aureus, Streptococcus faecalis* and *Enterobacter cloacae*. The amine hydrofluorides according to the invention in particular inhibit the sugar degradation in acid-producing plaque bacteria and, owing to the formation of a hydrophobic film, increase the acid resistance of the hard tooth substance and thus have caries-prophylactic action. They also favour the remineralization of initial carious lesions.

The amine hydrofluorides according to the invention contain straight-chain (i.e. unbranched) hydrocarbon residues. They can have hydrocarbon residues with both an even- and odd-numbered chain length. Residues having an even-numbered chain length are preferred with regard to physiological acceptability. The residues can preferably be fully saturated or mono-, di- or polyunsaturated. Examples of saturated hydrocarbon residues having an even-numbered chain length are decyl, dodecyl (lauryl), tetradecyl (myristyl), hexadecyl (cetyl, palmityl), octadecyl (stearyl) and eicosanyl. Examples of unsaturated residues having an even-numbered chain length are 9-cis-octadecenyl (oleyl), 9-trans-octadecenyl (elaidyl), cis,cis-9,12-octadecadienyl (linolyl), cis,cis,cis-9,12,15-octadecatrienyl (linolenyl) or 9-cis-eicosaenyl (gadolyl). Lauryl, myristyl, cetyl, oleyl and stearyl residues are preferred.

The amine hydrofluorides are prepared according to the invention by reacting an amine of the general formula (II):

R—N(CH$_2$CH$_2$OH)$_2$ (II)

in which R is a hydrocarbon residue having 10 to 20 carbon atoms, with hydrogen fluoride. The reaction can be carried out in all solvents which have an adequate solubility for the free amine of the formula (II) and are not attacked by hydrogen fluoride. Examples of suitable solvents are $C_1$- to $C_4$-alcohols and dimethyl sulfoxide: ethanol is particularly preferred. The addition of the hydrogen fluoride as an aqueous solution, i.e. as hydrofluoric acid, is preferred. The hydrogen fluoride is preferably added in an amount from 1 to 5, particularly preferably from 1.0 to 1.1, equivalents, based on the amine. The temperature of the reaction is not critical and can in general be between −10 and +100° C., whereby the upper limit may be given by the boiling point of the solvent, or the lower limit by the melting point of the solvent. The preferred temperature of the reaction is between 25° C. and 40° C. After the completion of the addition of the hydrogen fluoride, the reaction mixture can be evaporated and dried, by means of which the amine hydrofluoride according to the invention is obtained. A possible small hydrogen fluoride loss during the evaporation and drying can be compensated by subsequent addition of a corresponding amount of hydrofluoric acid in the preparation of the formulations according to the invention.

The amine of the formula (II) can be prepared in a manner which is known or known per se by hydroxyethylation of a primary amine R—NH$_2$, in which R has the above meaning, with ethylene oxide (oxirane), the ethoxylation taking place virtually quantitatively only on the nitrogen atom.

The primary amine R—NH$_2$ can be obtained in a known manner from a fatty acid of the formula R—COOH, in which R has the above meaning, by means of the synthesis steps amide formation/dehydration/catalytic reduction, as are also used in the synthesis of the already-known olaflur. Suitable fatty acids or fatty acid mixtures of the formula R—COOH and suitable amines or amine mixtures of the formula R—NH$_2$ are known and in some cases obtainable commercially.

According to a further variant, the amine of the formula (II) can be prepared by alkylation of diethanolamine in a nucleophilic S$_N$2 substitution:

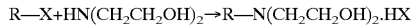

R—X+HN(CH$_2$CH$_2$OH)$_2$→R—N(CH$_2$CH$_2$OH)$_2$.HX where R—X is the alkylating agent, R has the same meaning as in formula (II) and X is, for example, chlorine, bromine or iodine.

The amine of the formula (II) is first obtained here as an ammonium salt. This ammonium salt is deprotonated using a base, for example aqueous NaOH, and then reacted according to the invention with hydrogen fluoride.

The alkylating agent R—X can be obtained from a corresponding, commercially obtainable fatty alcohol by introducing a leaving group:

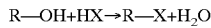

R—OH+HX→R—X+H$_2$O where R—OH is the fatty alcohol, and HX is, for example, hydrogen chloride, hydrogen bromide or hydrogen iodide.

A separation of possible homologues and/or double bond isomers can be carried out at the stage of the fatty alcohol, e.g. by fractional distillation and/or recrystallisation, so that a pure fatty alcohol is obtained (for the necessary physical data cf., for example, Römpp, Chemielexikon [Chemical Encyclopedia], 9th Edition, Vol. 2, page 1337).

The amine hydrofluorides according to the invention are preferably essentially free of di- or polyamine hydrofluorides, such as are typical of the already-known olaflur. They are free, in particular if the preparation route via the alkylation of highly pure diethanolamine is selected, of products in which the amino groups are over- or under-hydroxyethylated (i.e. in that the amines are quaternary or secondary after the hydroxyethylation) or the hydroxyethyl groups are etherified. The amine hydrofluorides according to the invention have a degree of hydroxyethylation of exactly two, if the route via the alkylation of diethanolamine is selected.

According to the invention, the object is also achieved by an amine hydrofluoride mixture comprising two or more compounds of the formula (I).

The mixtures of amine hydrofluorides according to the invention can be mixtures in any desired ratio of two or more amine hydrofluorides which can be prepared according to one of the above processes.

Mixtures of amine hydrofluorides are preferred which have been obtained from a fatty acid mixture of an animal or vegetable fat or oil and whose hydrocarbon residues R therefore have a frequency distribution dependent on the chain length which reflects the frequency distribution of the corresponding fatty acid homologues in this fatty acid mixture. Such mixtures can be obtained by hydrofluoridation of mixtures of amines of the formula (II). The mixtures of amines are prepared here, starting from an animal or vegetable fat or oil, using the synthesis steps hydrolysis/amide formation/dehydration/catalytic reduction/hydroxyethylation in analogy to the corresponding synthesis steps for the already-known olaflur.

Examples of the vegetable oils or fats suitable for these mixtures of amines of the formula (II) are almond oil, avocado pear oil, maize germ oil, cottonseed oil, rapeseed oil, linseed oil, olive oil, peanut oil, pumpkin seed oil, rice bran oil, safflower oil, sesame oil, soya oil, sunflower oil, wheatgerm oil, babassu oil, coconut oil, palm kernel oil, rape oil and palm oil. Examples of animal fats or oils are bovine tallow, chicken fat, goat's fat, pork dripping, sheep tallow, various fish oils and whale oil. A preferred animal fat is bovine tallow: preferred vegetable oils are soya oil, rape oil or soya oil/rape oil mixtures. A detailed table with the compositions of the fatty acid mixtures resulting from these animal or vegetable fats or oils is found, for example, in Ullmann's Encyclopaedia of Industrial Chemistry 5th Edition, Vol. A10, page 176 et seq. The amounts of saturated fatty acids can be increased, if desired, by catalytic hydrogenation.

Mixtures of amines of the formula (II) which have been obtained from a vegetable or animal fat or oil are obtainable commercially. Examples are the products Ethomeen S/12 (obtained from the fatty acid mixture from soya oil), Ethomeen T/12 and Ethomeen HT/12 (both obtained from the fatty acid mixture from bovine tallow, the latter being hydrogenated) marketed by AKZO NOBEL. The main component in S/12 and T/12 is N-oleyldiethanolamine. The applicant was also able to order a mixture of amines of the formula (II), whose main component is N-stearyldiethanolamine, from WITCO. This mixture is obtained from the fatty acid mixture of bovine tallow, the oleyl residues being hydrogenated to give stearyl residues.

A mixture of amine hydrofluorides according to the invention can also be obtained if a mixture of amine hydrofluorides which has been obtained from the fatty acid mixture of a vegetable or animal fat or oil is mixed with one or more pure amine hydrofluorides. Two or more mixtures of amine hydrofluorides which have been obtained from different fats or oils in each case can also be mixed.

A fat such as is known in the art can also be reduced to a mixture of fatty alcohols, and this fatty alcohol mixture can be processed, as described above for the synthesis of amine hydrofluorides in pure form from pure fatty alcohols, to give a corresponding mixture of amine hydrofluorides.

The invention likewise relates to oral hygiene compositions comprising at least one of the amine hydrofluorides according to the invention in an efficacious amount. They can be prepared in analogy to the conventional oral hygiene compositions and using the customary auxiliaries and additives.

Preferably, the oral hygiene compositions according to the invention can also contain a mixture of amine hydrofluorides obtained from a vegetable or animal oil or fat, in particular from bovine tallow, soya oil, rape oil or soya oil/rape oil mixtures.

In addition to an amine hydrofluoride or a mixture of amine hydrofluorides, oral hygiene compositions according to the invention can also preferably contain tin(II) fluoride. These tin fluoride-containing oral hygiene compositions are active against gingivitis, parodontitis and stomatitis, likewise being caries-prophylactically active due to the content of amine hydrofluorides. In such oral hygiene compositions, the amine hydrofluoride(s) according to the invention bring about a pharmaceutical stabilization of the Sn(II) against precipitation to give insoluble tin(IV) oxide.

The lower limit for the content by weight of the amine hydrofluoride(s) in the oral hygiene composition is determined by the still-significant prophylactic action, i.e. in particular the antimicrobial or caries-prophylactic action. The upper limit for the weight of the amine hydrofluoride(s) is not critical, it should, however, not be too high with respect to possible toxic side effects.

In the case of an oral hygiene composition in the form of toothpastes, it is possible for amine hydrofluorides according to the invention preferably to be contained in amounts from 0.02 to 5% by weight, particularly preferably from 2 to 3% by weight.

The additives and auxiliaries for toothpastes according to the invention are scouring agents, binding agents, plasticizers, moisturizing agents and also flavourings and aromatic substances. Examples of scouring agents are alkaline earth metal phosphates (e.g. dicalcium phosphate dihydrate, dicalcium phosphate anhydride, tricalcium phosphate), insoluble alkali metal metaphosphates, finely ground or colloidal silicas, aluminium hydroxide hydrates, aluminium silicates, aluminium magnesium silicates and alkaline earth metal carbonates. Suitable plastics, e.g. polyethylene, can also be employed. These scouring agents are customarily employed in amounts of 20 to 60% by weight. Binding agents are gelling agents of natural or synthetic origin. Examples of these are water-insoluble alginates, carraghenates, guar gum, tragacanth, water-soluble cellulose ethers (e.g. methylcellulose, hydroxyalkylcelluloses, carboxymethylcellulose), water-soluble salts of polyacrylic acids (Carbopols), aerosils and bentonites. In general, the content of the binding agents is 0.5 to 10% by weight. Examples of plasticizers and moisturizing agents are polyhydric alcohols such as glycerol, propylene glycol, sorbitol, mannitol, glucose syrup, polyethylene glycols, polypropylene glycols and polyvinylpyrrolidone. They are customarily employed in amounts from 10 to 40% by weight. Examples of flavourings are saccharin, quaternary ammonium saccharinates, cyclamates, coumarin and vanillin. Aromatic substances are customarily ethereal oils, e.g. peppermint oil, spearmint oil, aniseed oil, menthol, anethole, citrus oil etc. or other essences such as apple, eucalyptus or spearmint essence.

Rinsing solutions according to the invention are preferably aqueous, alcoholic or mixed aqueous/alcoholic solutions with one or more of the amine hydrofluorides according to the invention. It is possible for the amine hydrofluoride(s) according to the invention to be present in amounts from 0.02 to 2% by weight, preferably 0.2 to 0.3% by weight. Additives and auxiliaries for rinsing solutions, are, for example, the abovementioned flavourings and aromatic substances, but also emulsifiers, wetting agents, sorbitol, xylitol and various drug extracts.

As the carrier material, dental gels according to the invention contain a swollen mixture of natural or synthetic hydrocolloids. Examples of these are methylcellulose, hydroxyalkylceluloses, carboxymethylcellulose, water-soluble and swellable salts of the polyacrylic acids, alginates, carraghenates and guar gum. The abovementioned flavourings and aromatic substances and moisturizing agents and possibly also pigments can also be admixed in small amounts into the respective gel base. It is possible for one or more of the amine hydrofluorides according to the invention to be contained in amounts from 0.02 to 10% by weight, preferably 4.9 to 5.0% by weight. To conceal the taste and/or as an additional fluoride source, it is also possible to add sodium fluoride, in amounts up to 5% by weight.

Further examples of oral hygiene compositions according to the invention are topical application solutions and chewable tablets. The content of amine hydrofluorides in topical application solutions can alternatively be higher than in rinsing solutions. In topical application solutions it can typically be 5 to 25% by weight, preferably 15 to 25% by weight. The same substances can be used as additives in topical application solutions as in the rinsing solutions. In the case of chewable tablets, amine hydrofluoride contents of typically 0.3 to 12% by weight, preferably 2 to 7% by weight, can be present. Additives for chewable tablets are binding agents and sucrose, glucose, lactose or preferably the non-cariogenic sugar types such as xylitol, mannitol or sorbitol. They can be improved in flavour by addition of aromatic substances. For the production of chewable tablets according to the invention, processes and tabletting presses known from the conventional production of chewable tablets can be employed.

In all oral hygiene compositions according to the invention, tin(II) fluoride can also be added in amounts of, as a rule, 0.001 to 2% by weight, as a solid or as, for example, an aqueous solution. The same additives and auxiliaries can be employed as in the tin fluoride-free oral hygiene compositions. As solutions of tin(II) fluoride are stabilized by addition of the amine hydrofluorides according to the invention, such solutions remain clear over a longer period and no cloudiness occurs. Combinations of the amine hydrofluorides according to the invention and tin(II) fluoride are therefore particularly suitable for use in oral hygiene compositions in the form of rinsing solutions. Rinsing solutions which contain efficacious amounts of one or more amine hydrofluorides and tin(II) fluoride are a preferred embodiment of the oral hygiene compositions according to the invention.

The present invention is now illustrated further by the following examples. All quantitative data in per cent, ppm and parts relate, if not mentioned otherwise, to weights.

EXAMPLE 1

Preparation of Amine Hydrofluorides

A weighed amount of a mixture of amines of the formula (II) (Ethomeen T/12 from AKZO NOBEL, typical distribution of the chain length of R: 1% $C_{12}$, 4% $C_{14}$, 31% $C_{16}$, 64% $C_{18}$) was placed into a suitable reaction vessel having a stirrer, homogenizer, temperature control with temperature indicator, vacuum equipment and an HF-resistant metering device, this amount being selected such that the filling of the vessel was at most 10 to 20% by volume. The mixture was dissolved in two parts of ethanol at room temperature. 1.015 equivalents of hydrogen fluoride were added from the metering device in the form of 40% strength aqueous hydrofluoric acid. Care was taken here that the temperature of the mixture did not exceed 40° C. The metering device was then rinsed out with the same volume of distilled water. The mixture was evaporated to dryness by careful evacuation (foam formation) and a maximum mixture temperature of 65° C.

The mixture of amine hydrofluorides prepared here is designated in the following as "oleyl amine fluoride".

EXAMPLE 2

Preparation of Amine Hydrofluorides

The procedure was as in Example 1, except that the starting mixture was another mixture of amines of the formula (II) (Ethomeen HT/12 from AKZO NOBEL, typical distribution of the chain length of R: 1% $C_{12}$, 4% $C_{14}$, 31% $C_{16}$, 64% $C_{18}$; essentially saturated by hydrogenation) instead of Ethomeen T/12.

For the mixture of amine hydrofluorides prepared here, the term "stearyl amine fluoride" is used in the following.

EXAMPLE 3

Toothpaste

The reaction container used was a mixer with a homogenizer. 62 g of stearyl amine fluoride from Example 2 (corresponding to 2.48% of the finished toothpaste) were added to the mixer and dissolved in 1.097 kg of water at 55° C. 600 g of 70% sorbitol, 37.5 g of peppermint essence, 625 g of silica gel, 50 g of hydroxyethylcellulose (Tylose H 10,000 P, Hoechst), 25 g of titanium dioxide and 3.75 g of saccharin were then added. The mixture was stirred at 100 rpm and level 1 of the homogenizer for 50 minutes at 35° C. and a pressure of 0.5 bar, then for a further 15 minutes at room temperature and a pressure of 0.1 bar.

EXAMPLE 4

Toothpaste

The reaction container used was a mixer having a homogenizer. 61.63 g of oleyl amine fluoride from Example 1 (corresponding to 2.465% of the finished toothpaste) were added to the mixer and dissolved in 0.5 kg of water at room temperature. 1.22 g of 42.21% strength hydrofluoric acid, 600 g of 70% sorbitol, 37.5 g of peppermint essence, 596 g of water, 625 g of silica gel, 50 g of hydroxyethylcellulose (Tylose H 10,000 P, Hoechst), 25 g of titanium dioxide and 3.75 g of saccharin were then added. The mixture was stirred at 100 rpm and level 1 of the homogenizer for 60 minutes at 35° C. and a pressure of 0.5 bar, then for a further 15 minutes at room temperature and a pressure of 0.1 bar.

EXAMPLE 5

Toothpaste

The reaction container used was a mixer with a homogenizer. 69.5 g of stearyl amine fluoride from Example 2 (corresponding to 2.78% of the finished toothpaste) were added to the mixer and dissolved in 1.014 kg of water at 55° C. 750 g of 70% sorbitol, 30 g of eucalyptus essence, 325 g of polyethylene, 175 g of silica gel, 10 g of saccharin, 47.5 g of hydroxyethylcellulose (Tylose H 10,000 P, Hoechst), 25 g of titanium dioxide and a solution of 3.75 g of NaOH in 50 g of water were then added. The mixture was stirred at 100 rpm and level 1 of the homogenizer for 60 minutes at 32° C. and a pressure of 0.6 bar, then for a further 15 minutes at room temperature and a pressure of 0.1 bar.

EXAMPLE 6

Toothpaste

The reaction container used was a mixer with a homogenizer. 69.0 g of oleyl amine fluoride from Example 1 (corresponding to 2.761% of the finished toothpaste) were added to the mixer and dissolved in 0.5 kg of water at room temperature. 1.36 g of 42.21% strength hydrofluoric acid, 750 g of 70% sorbitol, 30 g of eucalyptus essence, 513 g of water, 325 g of polyethylene, 175 g of silica gel, 10 g of saccharin, 47.5 g of hydroxyethylcellulose (Tylose H 10,000 P, Hoechst) and 25 g of titanium dioxide and a solution of 3.75 g of NaOH and 50 g of water were then added. The mixture was stirred at 100 rpm at level 1 of the homogenizer for 65 minutes at 38° C. and a pressure of 0.6 bar, then for a further 15 minutes at 25° C. and a pressure of 0.1 bar.

EXAMPLE 7

Rinsing Solution

The preparation was carried out under nitrogen protective gas. 2.48 g of stearyl amine fluoride from Example 2, (corresponding to 0.248% of the finished rinsing solution) were dissolved in 918 g of water at 50° C. in a reaction vessel. 2 g of PEG-40-hydrogenated castor oil (Cremophor RH 410, BASF), 50 g of ethanol, 1 g of peppermint/spearmint essence, 25 g of xylitol, 250 mg of Acesulfam K, 0.5 g of 0.4% strength pigment solution of Ariavit Blue 3.85 CI 42051 were then added and dissolved.

EXAMPLE 8

Rinsing Solution 0.575 g of tin(II) fluoride were additionally added to a rinsing solution prepared according to the recipe of Example 7 and dissolved.

EXAMPLE 9

Rinsing Solution

The preparation was carried out under nitrogen protective gas. 25 g of xylitol and 0.5 g of 0.4% strength pigment solution of Ariavit Blue 3.85 CI 42051 were dissolved in 918 g of water in a reaction vessel. 2.47 g of oleyl amine fluoride from Example 1 (corresponding to 0.247% of the finished rinsing solution), 2 g of PEG-40-hydrogenated castor oil (Cremophor RH 410, BASF), 50 g of ethanol, 1 g of peppermint/spearmint essence, 250 mg of Acesulfam K and 0.048 g of 42.2% strength hydrofluoric acid were then added and dissolved.

EXAMPLE 10

Rinsing Solution 0.556 g of tin(II) fluoride were additionally added to a rinsing solution prepared according to the recipe of Example 9 and dissolved.

EXAMPLE 11

Dental Gel

The reaction container used was a mixer with a homogenizer. 124 g of stearylamine fluoride from Example 2(corresponding to 4.96% of the finished dental gel) were added to the mixer and dissolved in 1.969 kg of water at 90° C. 45 g of peppermint/apple essence, 55.5 g of sodium fluoride, 10 g of saccharin, 250 g of propylene glycol and 46 g of hydroxyethylcellulose (Tylose H 10,000 P, Hoechst) were then added. The mixture was stirred at 100 rpm and level 1 of the homogenizer for 40 minutes at 30° C. and a pressure of 0.4 bar, then for a further 25 minutes at room temperature and a pressure 0.1 of bar.

EXAMPLE 12

Dental Gel

The reaction container used was a mixer with a homogenizer. 123 g of oleylamine fluoride from Example 1

(corresponding to 4.93% of the finished dental gel) were added to the mixer and dissolved in 1,000 kg of water. 2.4 g of 42.21% strength hydrofluoric acid, 45 g of peppermint/apple essence, 55.5 g of sodium fluoride, 10 g of saccharin, 250 g of propylene glycol and 46 g of hydroxyethylcellulose (Tylose H 10,000 P, Hoechst) were then added. Dilution was carried out with a further 968 g of water. The mixture was stirred at 100 rpm and level 1 of the homogenizer for 50 minutes at 30° C. and a pressure of 0.4 bar, then for a further 75 minutes at 25° C. and a pressure of 0.1 bar.

EXAMPLE 13

Chewable Tablet 15 parts of oleylamine fluoride were suspended in about 20 parts of water and subsequently granulated by spray drying (active compound granules). A mixture of 0.6 parts of saccharin, 3 parts of Plasdone (cross-linked polyvinylpyrrolidone), 7.5 parts of Avicel (native cellulose), 5 parts of talc, 48 parts of rice starch, 0.9 parts of peppermint oil and 220 parts of sorbitol were also granulated by spray drying (auxiliary granules). The active compound granules were mixed with the auxiliary granules in a gravity mixer and tableted to give a batch of chewable tablets in a commercially available eccentric press. The average weight per tablet was 300 mg.

EXAMPLE 14

Topical Application Solution 19.85 parts of oleyl amine fluoride, corresponding to 19.85% of the finished topical application solutions, 0.15 parts of saccharin, 2.5 parts of essence mixture (consisting for its part of 30 parts of aniseed oil, 7.5 parts of menthol, 1.0 parts of vanillin, 6.0 parts of spearmint oil and 55.5 parts of peppermint oil) and 77.5 parts of water were mixed. A ready-to-use topical application solution was obtained.

EXAMPLE 15

Measurement of the Total Fluoride Content of Amine Hydrofluoride Mixtures

A weighed amount of oleyl amine fluoride from Example 1 was dissolved in water and the fluoride content was determined by alkalimetric titration with 0.1N aqueous tetrabutylammonium hydroxide solution (assumption of equimolar amounts of fluoride and ammonium groups). Measurements showed a fluoride content of 4.28%. Analogously, a fluoride content of 5.04% was found for the stearyl amine fluoride of Example 2.

EXAMPLE 16

Measurement of the Total Fluoride Content of Toothpastes and Dental Gels

Measurement was carried out using a fluoride electrode and a measuring apparatus 610 from METROHM. The calibration of the electrode was carried out with a calibration solution of 45.24 ppm of fluoride, which was made up as follows:
a) 20 ml of fluoride standard solution in water (containing 200 mg of NaF/litre of solution),
b) 20 ml of TISAB buffer solution, pH 5.0 to 5.5.
The TISAB buffer was prepared here as follows:
Solution I: 5 g of Komplexon IV, 57 g of glacial acetic acid and 58 g of sodium chloride in 500 g of water;

Solution II: 32 g of NaOH in 350 g of water.
Solutions I and II were mixed and diluted to 1,000 ml with water.

The measuring solution of the sample was prepared by adjusting an accurately weighed amount of sample of approximately 1 g to 20 g with water and mixing with 20 g of TISAB buffer. The measuring solution was measured under the same conditions as the calibration solution. The calculation of the fluoride content of the sample was carried out by means of the general formula:

$$ppm\ F^- = 45.24 \times \frac{\text{sample solution measurement}}{\text{calibration solution measurement}} \times$$
$$= \frac{40\ g}{\text{weight of sample g}}$$

The total contents shown in Table 1 were found.

TABLE 1

| | |
|---|---|
| Toothpaste from Example 3 | 1243 ppm of $F^-$ |
| Toothpaste from Example 4 | 1170 ppm of $F^-$ |
| Toothpaste from Example 5 | 1432 ppm of $F^-$ |
| Toothpaste from Example 6 | 1390 ppm of $F^-$ |
| Dental gel from Example 11 | 1.25% $F^-$ |
| Dental gel from Example 12 | 1.32% $F^-$ |

EXAMPLE 17

Measurement of the Total Fluoride Content of Rinsing Solutions

Measurement was carried out using a fluoride electrode and a measuring apparatus 610 from METROHM. The calibration of the electrode was carried out with a calibration solution of 125 ppm of fluoride, which was made up as follows:
a) 20 ml of fluoride standard solution (250 ppm of fluoride) in fluoride-free rinsing solution,
b) 20 ml of TISAB buffer (cf. Example 16).
The measuring solution of the sample was prepared by mixing 20 ml of rinsing solution sample and 20 ml of TISAB buffer. The measuring solution was measured under the same conditions as the calibration solution. The calculation of the fluoride content of the sample was carried out by means of the general formula:

$$ppm\ F^- = 250 \times \frac{\text{sample solution measurement}}{\text{calibration solution measurement}}$$

The total contents shown in Table 2 were found.

TABLE 2

| | |
|---|---|
| from Example 9 | 250 ppm of $F^-$ |
| from Example 10 | 250 ppm of $F^-$ |

EXAMPLE 18

Determination of the Microbiological Activity of Amine Hydrofluorides against *Staphylococcus aureus* (ATCC 6538) and *Streptococcus faecalis* (ATCC 10541) in the Test for the Determination of the Minimum Inhibitory Concentration (MIC Test)

These two micro-organisms were selected because they are of importance as cocci representative of oral cavity cocci. Three stock solutions of one part by weight each of a bacteria-containing medium consisting of a so-called shaker culture based on Caso broth, adjusted to 100,000 bacterial cells/µl, and one part by weight each of three physiological saline solutions which contained oleyl amine fluoride from Example 1. (for stock solution A) or stearyl amine fluoride from Example 2 (for stock solution B) or already-known olaflur (for stock solution C) were prepared. The concentration of the amine hydrofluorides in the physiological saline solutions was such that a fluoride concentration of 3,000 ppm of F⁻/100 g of stock solution resulted in each finished stock solution. A geometric dilution series was formed from each stock mixture by diluting with physiological saline solution (dilution factor 2 in each case). It was investigated at which dilutions a significant inhibition of the micro-organisms was no longer observed. Table 3 shows the highest dilution stages compared with the stock mixtures at which the bacteria were still destroyed in an actual experiment.

TABLE 3

|  | compared with stock mixture A | compared with stock mixture B | compared with stock mixture C |
|---|---|---|---|
| *Staph. aureus* | 1:8192 | 1:2048 | 1:4096 |
| *Str. faecalis* | 1:8192 | 1:2048 | 1:8192 |

Taking into account the biological variability in the vitality of the bacteria, the three active substances are to be regarded as approximately equally active.

EXAMPLE 19

Determination of the Microbiological activity of toothpaste formulations against *Staphylococcus aureus* (ATCC 6538) and *Streptococcus faecalis* (ATCC.10541) in the MIC Test Three stock mixtures of one part by weight each of a bacteria-containing medium consisting of a shaker culture based on Caso broth, adjusted to 100,000 bacterial cells/µl and one part by weight of a toothpaste (stock mixture A: toothpaste from Example 3; stock mixture B: toothpaste from Example 4; stock mixture C: commercial toothpaste containing known olaflur) were prepared. The fluoride content by weight was equal in all the stock mixtures. A geometric dilution series of each stock mixture was formed by diluting with physiological saline solution (dilution factor 2 in each case). It was investigated at which dilutions a significant inhibition of the micro-organisms was no longer observed. Table 4 shows the highest dilution stages compared with the stock mixtures in which the bacteria were still destroyed in an actual experiment.

TABLE 4

|  | compared with stock mixture A | compared with stock mixture B | compared with stock mixture C |
|---|---|---|---|
| *Staph. aureus* | 1:512 | 1:4096 | 1:4096 |
| *Str. faecalis* | 1:256 | 1:4096 | 1:1024 |

Taking into account the biological variability in the vitality of the micro-organisms, the two toothpastes based on oleyl amine fluoride or olaflur exhibit comparable efficacy.

What is claimed is:

1. Amine hydrofluoride of the general formula (I):

$$R-N(CH_2CH_2OH)_2 \cdot HF \qquad (I)$$

in which R is a straight-chain hydrocarbon residue having 10 to 20 carbon atoms.

2. Amine hydrofluoride according to claim 1, wherein the hydrocarbon residue R has an even number of carbon atoms.

3. Amine hydrofluoride according to claim 1, wherein the hydrocarbon residue R is a lauryl, myristyl, cetyl, oleyl, linolyl, linolenyl, stearyl, eicosanyl or eicosaenyl residue.

4. An antibacterially active agent of the general formula (I):

$$R-N(CH_2CH_2OH)_2 \cdot HF \qquad (I)$$

in which R is a straight-chain hydrocarbon residue having 10 to 20 carbon atoms.

5. Amine hydrofluoride mixture comprising two or more compounds of the general formula (I):

$$R-N(CH_2CH_2OH)_2 \cdot HF \qquad (I)$$

in which R is a straight-chain hydrocarbon residue having 10 to 20 carbon atoms.

6. Mixture according to claim 5, obtained from the fatty acid mixture of a vegetable or animal fat or oil.

7. Mixture according to claim 5 or 6, obtained from bovine tallow, soya oil, rapeseed oil or a soya oilrapeseed oil mixture.

8. Process for the preparation of an amine hydrofluoride of the general formula (I):

$$R-N(CH_2CH_2OH)_2 \cdot HF \qquad (I)$$

in which R is a straight-chain hydrocarbon residue having 10 to 20 carbons atoms, comprising reacting an amine of the general formula (II):

$$R-N(CH_2CH_2OH)_2 \qquad (II)$$

in which R is a straight-chain hydrocarbon residue having 10 to 20 atoms, with hydrogen fluoride.

9. Oral hygiene composition, comprising at least one amine hydrofluoride of the general formula:

$$R-N(CH_2CH_2OH)_2 \cdot HF \qquad (I)$$

in which R is a straight-chain hydrocarbon residue having 10 to 20 carbon atoms, in an antimicrobially or caries-prophylactically efficacious amount, and a customary additive or auxiliary suitable for use in oral hygiene compositions.

10. Oral hygiene composition according to claim 9, comprising a mixture of amine hydrofluorides of the formula (I) obtained from bovine tallow, soya oil, rapeseed oil or a soya oil/rapeseed oil mixture.

11. Oral hygiene composition according to claim 9, in the form of a toothpaste and comprising one or more amine hydrofluorides of the formula (I) in an amount from 0.02 to 5, per cent by weight.

12. Oral hygiene composition according to claim 9, in the form of a rinsing solution and comprising one or more amine hydrofluorides of the formula (I) in an amount from 0.02 to 2, per cent by weight.

13. Oral hygiene composition according to claim 9, in the form of a dental gel and comprising one or more amine hydrofluorides of the formula (I) in an amount from 0.02 to 10, per cent by weight.

14. Oral hygiene composition according to claim 9 in the form of a topical application solution and comprising one or more amine hydrofluorides of the formula (I) in an amount from 5 to 25, per cent by weight.

15. Oral hygiene composition according to claim 9 in the form of a chewable tablet and comprising one or more amine hydrofluorides of the formula (I) in an amount from 0.3 to 12, per cent by weight.

16. Oral hygiene composition according to claim 9, further including tin (II) fluoride in an amount of up to 2% by weight.

17. A method of preparation of an oral hygiene composition, comprising admixing am amine hydrofluoride of the general formula (I):

$$R\text{—}N(CH_2CH_2OH)_2 \cdot HF \qquad (I)$$

in which R is a straight-chain hydrocarbon residue having 10 to 20 carbon atoms and a customary auxiliary or additive suitable for use in oral hygiene compositions.

18. A method of caries-prophylactic treatment of a tooth enamel, comprising applying an amine hydrofluoride of the general formula (I):

$$R\text{—}N(CH_2CH_2OH)_2 \cdot HF \qquad (I)$$

in which R is a straight-chain hydrocarbon residue having 10 to 20 carbons atoms, to said tooth enamel.

19. A method of treatment of gingivitis, periodontitis or stomatitis comprising orally administering an amine hydrofluoride of the general formula (I):

$$R\text{—}N(CH_2CH_2OH)_2 \cdot HF \qquad (I),$$

in which R is a straight-chain hydrocarbon residue having 10 to 20 carbon atoms, and tin (II) fluoride.

* * * * *